(12) United States Patent
Yared et al.

(10) Patent No.: US 10,123,851 B2
(45) Date of Patent: Nov. 13, 2018

(54) DENTAL IRRIGATION, CLEANING AND DEBRIDEMENT SYSTEM, DEVICE AND INSTRUMENT

(71) Applicants: Ghassan Yared, Toronto (CA); Gustavo De-Deus, Rio de Janerio (BR)

(72) Inventors: Ghassan Yared, Toronto (CA); Gustavo De-Deus, Rio de Janerio (BR)

( * ) Notice: Subject to any disclaimer, the term of this patent is extended or adjusted under 35 U.S.C. 154(b) by 0 days.

(21) Appl. No.: 15/529,032

(22) PCT Filed: Nov. 23, 2015

(86) PCT No.: PCT/CA2015/000584
§ 371 (c)(1),
(2) Date: May 23, 2017

(87) PCT Pub. No.: WO2016/082023
PCT Pub. Date: Jun. 2, 2016

(65) Prior Publication Data
US 2017/0258552 A1   Sep. 14, 2017

(30) Foreign Application Priority Data

Nov. 25, 2014 (CA) .................................... 2872261

(51) Int. Cl.
*A61C 5/50* (2017.01)
*A61C 5/40* (2017.01)
(Continued)

(52) U.S. Cl.
CPC .................. *A61C 5/50* (2017.02); *A61C 5/40* (2017.02); *A61C 17/0208* (2013.01); *A61C 17/30* (2013.01)

(58) Field of Classification Search
CPC ....... A61C 5/40; A61C 17/02; A61C 17/0202; A61C 17/0208
See application file for complete search history.

(56) References Cited

U.S. PATENT DOCUMENTS 6,079,979 A  *  6/2000  Riitano ................. A61C 17/02
                                                                    433/224
6,224,378 B1 *  5/2001  Valdes ................ A61C 1/0084
                                                                    433/224
(Continued)

FOREIGN PATENT DOCUMENTS

CA         2649905 A1    11/2007
WO     2005032393 A2     4/2005
(Continued)

OTHER PUBLICATIONS

O. A. Peters, K. Schoenenberger & A. Laib; Departments of Preventive Dentistry, Cariology and Periodontology; and Biomedical Engineering, ETH; University of Zurich, Zurich, Switzerland; Journal, 34, 221-230; published 2001; accessed May 5, 2017.

(Continued)

*Primary Examiner* — Ralph Lewis
(74) *Attorney, Agent, or Firm* — Black, McCuskey, Souers & Arbaugh, LPA

(57) ABSTRACT

A device for irrigating a canal during a root canal treatment or retreatment provides a fluid reservoir in fluid communication with at least one pump for delivering an irrigant under pressure. A hand-held wand has a proximal end for receiving the irrigant under pressure, permitted to flow through the wand head by an actuator. An irrigant delivery needle which affixed to the working end of the wand delivers irrigant through at least one irrigant dispersion orifice at a selected delivery angle and pressure. Aspirating means and/or shielding may optionally be provided.

14 Claims, 9 Drawing Sheets

(51) Int. Cl.
  *A61C 17/02* (2006.01)
  *A61C 17/30* (2006.01)

(56) References Cited

U.S. PATENT DOCUMENTS

| | | | | |
|---|---|---|---|---|
| 6,497,572 | B2* | 12/2002 | Hood | A61C 1/0084 433/81 |
| 6,971,878 | B2* | 12/2005 | Pond | A61C 5/40 433/81 |
| 8,753,121 | B2* | 6/2014 | Gharib | A61C 17/02 433/224 |
| 2003/0207231 | A1* | 11/2003 | Nance | A61C 5/40 433/81 |
| 2007/0248932 | A1* | 10/2007 | Gharib | A61C 17/02 433/81 |
| 2011/0117517 | A1* | 5/2011 | Bergheim | A61C 5/02 433/81 |

FOREIGN PATENT DOCUMENTS

| | | |
|---|---|---|
| WO | 2011060327 A1 | 5/2011 |
| WO | WO 2014/116886 A2 | 7/2014 |

OTHER PUBLICATIONS

P.N.R. Nair, Stephane Henry, Victor Cano, and Jorge Vera; "Microbial status of apical root canal system of human mandibular first molars with primary apical periodontitis after "one-visit" endodontic treatment"; vol. 99, No. 2 published Feb. 2005; accessed May 5, 2017.

Patricia Britto, Leticia Souza, Julio Machado De Oliviera, Flavio Alves, Gustavo De Deus, Helio Lopes, and Jose Siqueira; "Comparison of the Effectiveness of Three Irrigation Techniques in Reducing Intracanal Enterococcus faecalis Populations: An In Vitro Study"; Estacio de Sa University, Faculty of Dentistry; vol. 35, No. 10; Brazil; published Oct. 2009; accessed May 5, 2017.

Gustavo De-Deus, Bianca Barino, Renata Zamolyi, Erick Souza, Albino Fonseca, Sandra Fidel, and Rivail Fidel; "Suboptimal Debridement Quality Produced by the Single-file F2 Protaper Technique in Oval-shaped Canals"; Veiga de Almeida University, vol. 36, No. 11; Brazil; published Nov. 2010; accessed May 5, 2017.

K. Gulabivala, Y-L Ng, M Gilbertson, and I Eames; "The fluid mechanics of root canal irrigation"; Institute of Pyhsics and Engineering in Medicine; printed in UK, 2010; doi: 10.1088/0967-3343/31/12/R01; accessed May 5, 2017.

Ove Peters, Claudia Boessler, Frank Paque; Root Canal Preparation with a Novel Nickel-Titanium Instrument Evaluated with Micro-computed Tomography: Canal Surface Preparation over Time:; American Association of Endodontists; vol. 36, No. 6; Jun. 2010; accessed May 5, 2017.

Marco Versiani, Jesus Pecora, Manoel De Sousa-Neto; "Flat-Oval Root Canal Preparation with Self-Adjusting File Instrument: A Micro—Computed Tomography Study"; American Association of Endodontists; vol. 37, No. 7; Jul. 2011; accessed May 5, 2017.

Jorge Vera, Jose Siqueira, Domenico Ricucci, Simona Loghin, Nancy Fernandez, Belina Flores, and Alvaro Cruz; "One- versus Two-visit Endodontic Treatment of Teeth with Apical Periodontitis: A Histobacteriologic Study"; American Association of Endodontists; vol. 38, No. 8; Aug. 2012; accessed May 5, 2017.

Supplementary European Search Report; 2 pages.

* cited by examiner

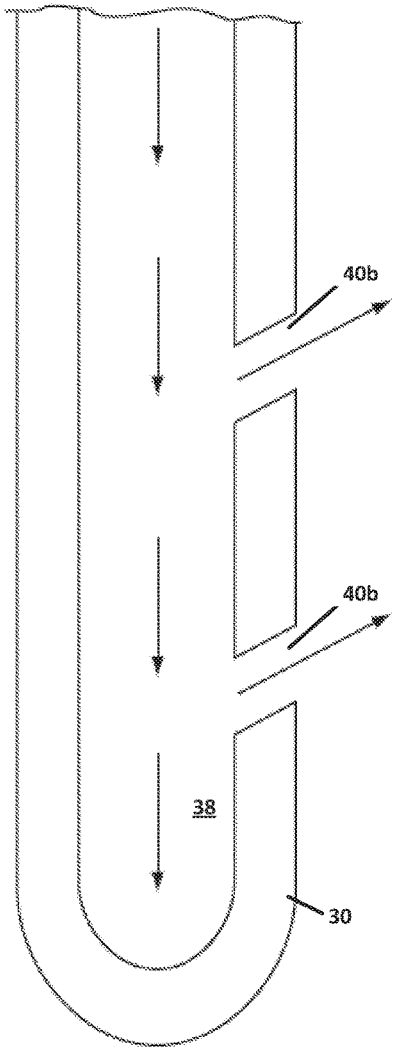
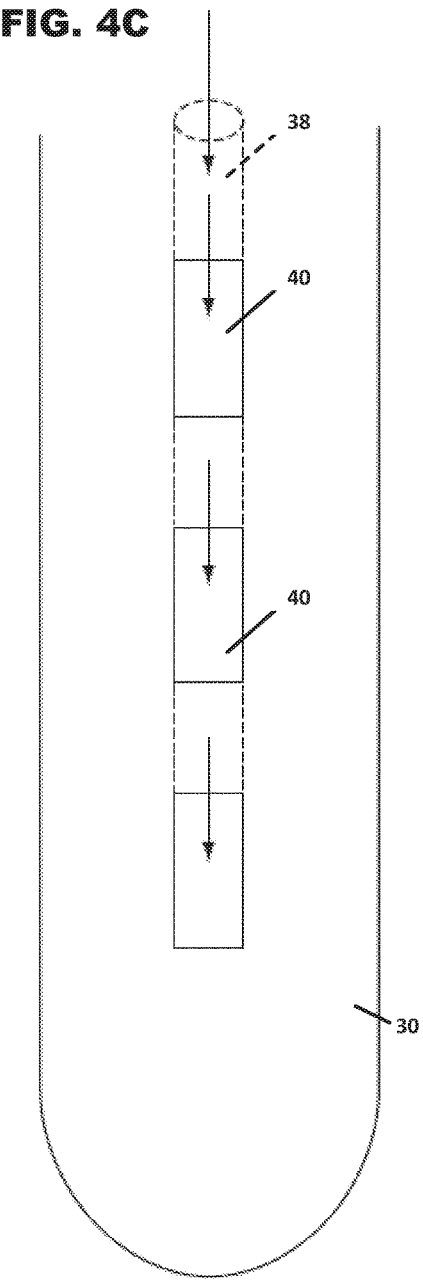

DENTAL IRRIGATION, CLEANING AND DEBRIDEMENT SYSTEM, DEVICE AND INSTRUMENT

FIELD OF THE INVENTION

This invention relates to dental irrigation, cleaning and debridement systems.

BACKGROUND OF THE INVENTION

An important endodontic procedure, known as a "root canal" procedure, involves removing organic material from the root canals of an infected tooth and filling the canal with an inert obturating material such as gutta percha gum.

An effective root canal procedure avoids extraction of the infected tooth. In this procedure, a dentist or endodontist utilizes a series of endodontic instruments, for example files, for the debridement, cleaning and sterilization of the root canal. These files are rotated within the canal to clean the canal surfaces, removing debridement (organic) material in the process, facilitating improved irrigation, and in some cases shaping the canal for easier filling with the obturating material.

The purpose of a canal preparation is to remove all organic debris and infected material from within the canal. The canal preparation is widely accomplished with engine-driven instruments. During the canal preparation, an irrigant is dispensed in the canal in order to help removing the debris created by the abrading action of endodontic instruments, and also promoting disinfection of the root canal space by flushing out microbes. The irrigant may be water or a chemical solution, or a combination thereof.

Once the pulp has been removed from the root canal, a smear layer remains. The smear layer is potentially infected, and its removal allows more efficient penetration of intra-canal medications into the dentinal tubules and a better interface between the filling material and the root canal walls. A final flush with chelating agents and antiseptic irrigating solutions is needed to remove the smear layer. However, the effectiveness of these chelating agents and antiseptic irrigating solutions remains limited especially in areas with a complex anatomy such as isthmuses. Therefore, the improvement of irrigating protocols is essential during root canal treatment in order to achieve better cleaning efficiency.

Numerous techniques and irrigating solutions have been described to accomplish the final irrigation. However, due to the complexity of the root canal anatomy, typically at least 40% of the root canal surface remains untouched by the endodontic instruments and unaffected by the irrigants, as shown in several high-definition micro-computed tomography and histological studies, respectively: Peters et al. 2001; Pape et al. 2010; Versiani et al. 2011, 2013, De-Deus et al. 2010; each of which is incorporated by reference in its entirety. Organic and infected debris always remain in the canal space (Vera et al. 2012). Most importantly, the organic inner layer of dentine (called "predentine") covering the wall of the root canal, which is usually heavily infected, will typically be untouched by endodontic instruments and irrigant. The remaining infected debris and the untouched infected predentine layer might adversely affect the final outcome of the root canal treatment; the bacteria remaining in the obturated canal space will use the organic material for nutrition and will re-colonize the obturated canal space leading to a failed root canal treatment (Nair et al. 2005).

The ability of an irrigant to act in these hard-to-reach areas depends mainly on the delivery method. See for example: Brito P R 1, Souza L C, Machado de Oliveira J C, Alves F R, De-Deus G, Lopes H P, Siqueira J F Jr. Comparison of the effectiveness of three irrigation techniques in reducing intracanal *Enterococcus faecalis* populations: an in vitro study. J Endod. 2009 October; 35(10):1422-7; De-Deus G, Barino B, Zamolyi R Q, Souza E, Fonseca A Jr, Fidel S, Fidel R A. Suboptimal debridement quality produced by the single-file F2 ProTaper technique in oval-shaped canals. J Endod. 2010 November; 36(11):1897-900; Gulabivala K, Ng Y L, Gilbertson M, Eames I. The fluid mechanics of root canal irrigation. Physiol Meas. 2010 December; 31(12): R49-84; Nair P N 1, Henry S, Cano V, Vera J. Microbial status of apical root canal system of human mandibular first molars with primary apical periodontitis after "one-visit" endodontic treatment. Oral Surg Oral Med Oral Pathol Oral Radiol Endod. 2005 February; 99(2):231-52; Peters O A, Sch8nenberger K, Laib A. Effects of four Ni—Ti preparation techniques on root canal geometry assessed by micro computed tomography. Int Endod J. 2001 April; 34(3):221-30; Peters O A, Boessler C, Paque F. Root canal preparation with a novel nickel-titanium instrument evaluated with micro-computed tomography: canal surface preparation over time. J Endod. 2010 June; 36(6):1068-72; Vera J, Siqueira J F Jr, Ricucci D, Loghin S, Fernandez N, Flores B, Cruz A G. One-versus two-visit endodontic treatment of teeth with apical periodontitis: a histobacteriologic study. J Endod. 2012 August; 38(8):1040-52; Versiani M A, Pecora J D, de Sousa-Neto M D. Flat-oval root canal preparation with self-adjusting file instrument: a micro-computed tomography study. J Endod. 2011 July; 37(7):1002-7.

As noted above, one important object of conventional canal preparation and irrigation procedures is to clean the canal (remove the organic and infected material and the organic predentine layer). In order to achieve this objective, a series of endodontic instruments are used to enlarge the root canal space in a continuously tapered shape. The instruments used toward the end of the canal preparation have relatively large diameters and tapers, and are relatively rigid. The use of these larger instruments has been associated with several complications such as instrument fracture, canal ledging and transportation, root perforation and weakening of the tooth structure (potentially leading to root fracture), which can ultimately lead to the need to extract the tooth. Moreover, conventional mechanical enlargement techniques embrace long-standing learning curves in order to achieve the minimal standard in terms of efficacy and safety.

There is accordingly a need for an improved irrigation system and device that provides greater cleaning and disinfecting efficacy in a root canal.

BRIEF DESCRIPTION OF THE DRAWINGS

In drawings which illustrate by way of example only a preferred embodiment of the invention.

FIGS. 4A, 4B and 4C are cross-sectional elevations of the tips of different embodiments of irrigating instruments for the device of the invention.

DETAILED DESCRIPTION OF THE INVENTION

Figure 1:
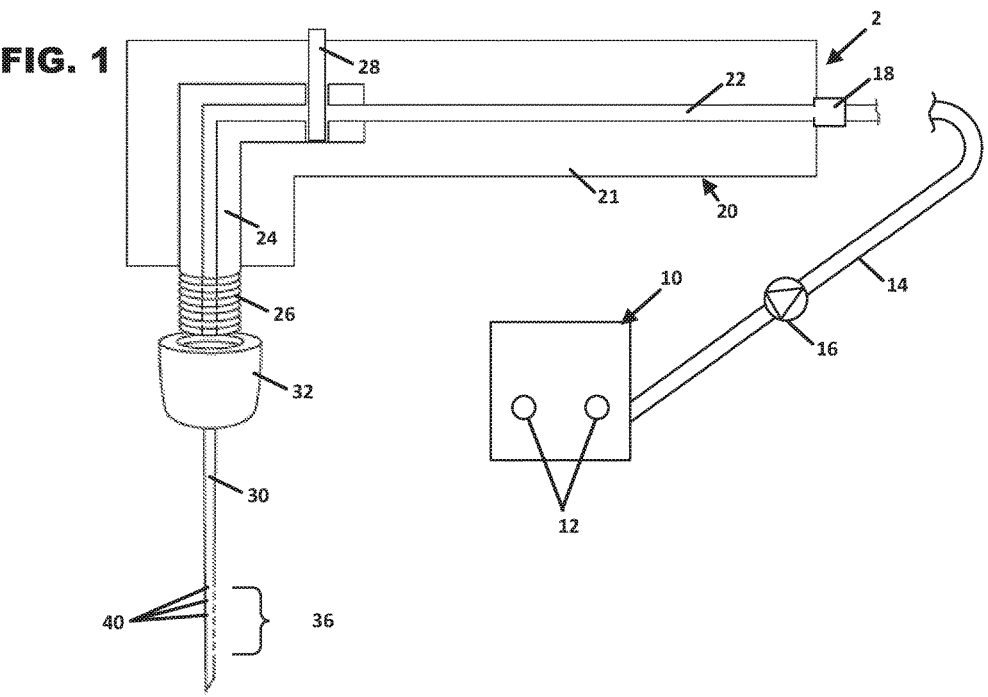
FIG. 1 is a cross-sectional elevation of a hand-held irrigation device in accordance with an embodiment of the invention.

The present invention relates to an endodontic cleaning and debridement device that delivers an irrigant under high pressure through a needle placed inside the canal space during a root canal procedure.

In certain embodiment benefits of the present invention in comparison to conventional procedures include that the device of the invention delivers much larger volumes of irrigants; delivers the irrigant in the canal under high pressure, which will allow the irrigant to penetrate and act in the hard-to-reach areas, flushing out remaining debris and removing the infected predentine layer so that the canal will be significantly cleaner, better disinfected and debrided before filling; and allows for a safer, faster and less costly canal preparation procedure. Moreover, these advantages can be obtained without creating any greater risk of fracture or potential complications than a conventional root canal treatment or retreatment procedure, and in some canal anatomies with a significantly lesser risk thereof. It will be appreciated that not all of the various advantages of the invention apply to all embodiments or to all canal anatomies.

Using a device according to the invention only a minimal canal enlargement is needed, which can be shaped in a continuous taper by endodontic instruments having smaller diameters and tapers. Further canal enlargement by larger instruments to improve disinfection, and to remove the infected pulpal tissue and predentine layer, is not needed because this stage is effected by a soft and thinner mechanical action of the irrigant under high pressure in the canal space. Therefore, the weakening of the overall tooth structure after canal preparation (which is a major and current concern for dental practitioners) is considerably mitigated. Also, the incidence of trans-operative complications such as instrument fracture, canal transportation, ledging and root perforation, which usually happen by the usage of larger instruments, will be significantly mitigated. The technique of canal preparation will cost the dental practitioner (an endodontist or dentist, for example) and patient less, because fewer endodontic instruments will be used in the procedure, which is also significantly faster and less onerous for the dentist.

Thus, in medium and large canals, the device of the invention will allow mechanical debridement with no usage need of the conventional endodontic files to accomplish the required shaping and cleaning of the canal space. The device of the invention allows for more efficient and thorough removal of the pulpal tissue, debris, infected material and predentine layer without the use of any endodontic instruments. The risk of instrument fracture, canal ledging, root perforation and root weakening is significantly reduced.

The system and device of the invention is thus able to debride root dentin, replacing the use of conventional instruments for this part of the procedure. The device of the invention can be used to cut additional dentine, as needed, by increasing the pressure of the irrigant delivery in the canal. Due to the delivery needle design in the preferred embodiments of the invention, in contrast to the conventional canal preparation and irrigation techniques the device of the invention can prevent pushing infected debris out of the apex of the tooth. Consequently, the incidence and intensity of post-operative pain and swelling may decrease significantly.

An embodiment of a device 2 of the invention, illustrated in FIG. 1, comprises a pressurized irrigant reservoir (not shown) contained within a console 10, shown schematically in FIG. 1, that allows setting the flow rate of the irrigant and the pressure in the reservoir, for example via pushbuttons, sliders, control knobs or any other suitable adjusting switches 12 or combination thereof. The console 10 can be a conventional dental irrigant supply console, preferably having a positive displacement peristaltic pump (not shown) to prevent fluid retraction and thus avoid patient cross-contamination, for example Endodontic Irrigation Device sold by ReDent Nova under the trademark VATEA, delivering irrigant via tube 14 in fluid communication with the device 2 of the invention.

Optionally a pump 16, shown schematically in FIG. 1, may be interposed between the reservoir console 10 and the device 2 of the invention, depending on such factors as the distance between the reservoir console 10 and the work area, the location of the reservoir console 10, the manner of its connection to a dental chair internal water system, and pressure requirements, as will be well known to a person skilled in the art. The irrigant delivery tubing 14 is preferably high pressure flexible tubing capable of withstanding pressures within the upper limit of the console 10, or the pump 16 if used.

The proximal end of the irrigant delivery tubing 14 is connected to the reservoir within the console 10, and specifically the water reservoir therein, in fluid-tight relation. The distal end of the tubing 14 is connected in fluid-tight relation to an irrigant passageway 22 within the handgrip portion 21 of the hand-held wand 20, preferably via a quick-connect coupler 18 such as the MULTIflex (trademark) coupler sold by Kayo which provides an anti-retraction valve to prevent the backflow of contaminated water into the tubing 14. Any other suitable coupler may be used, or the tubing 14 may be permanently connected to the wand 20. If a pump 16 is used, the pump 16 is interposed into the tubing 14 in fluid-tight relation at any convenient position.

The other end of the hand-held wand 20 is configured to connect an irrigant delivery needle 30, an irrigant egress zone 36 of which will be positioned in the canal. The needle 30 is securely attached to the head of the wand 20, for example via a threaded male coupler portion 26 at the distal end of an elbow 24 embedded in the wand 20 complementary to a threaded female coupler portion 32 from which the needle 30 extends. The needle 30 may alternatively be affixed to the head of the wand 20 using a 'Luer-Lock' quick-connect system, or any other suitable coupler capable of withstanding the high pressures within the operating range of the device 2, with a suitable safety margin to prevent dislodgment during use.

Figure 2:
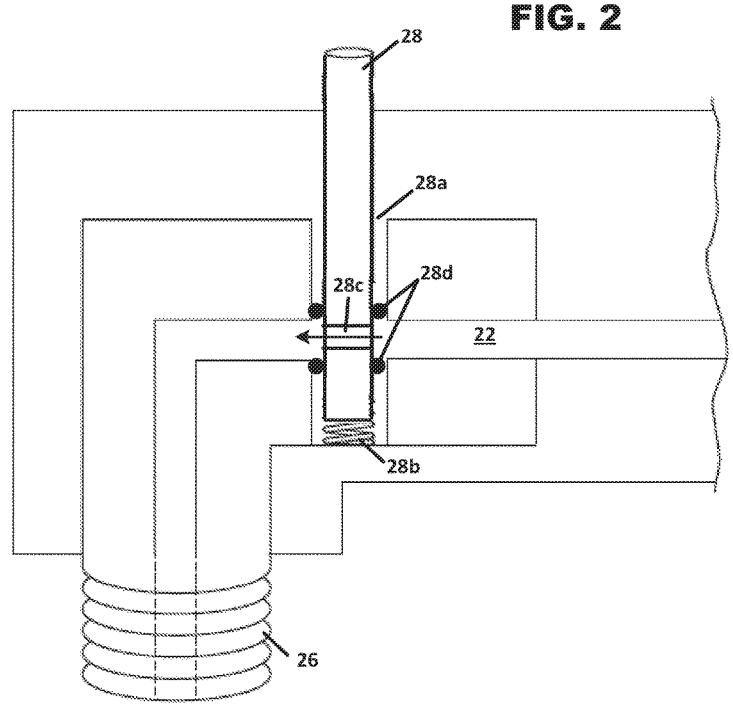
FIG. 2 is an enlarged cross-sectional elevation of the head of the irrigation device of FIG. 1.
Figure 3:
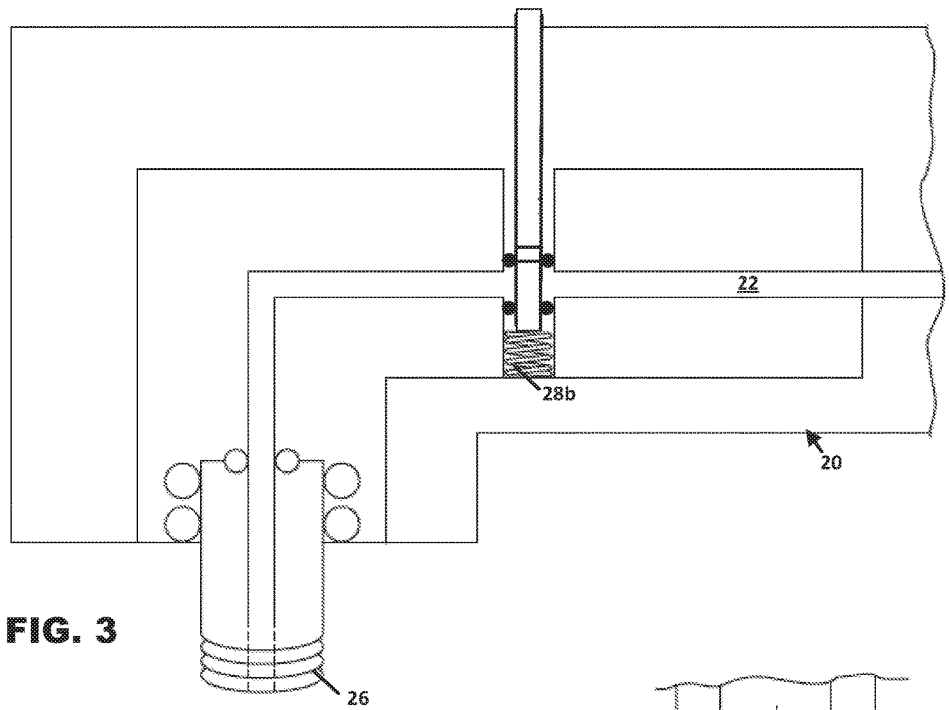
FIG. 3 is an enlarged cross-sectional elevation of the head of a further irrigation device in accordance with the invention.

The proximal end of the elbow 24 is connected to the tubing 14 in fluid-tight relation. The proximal end of the elbow 24 preferably provides a seat 28a for an actuator, in the embodiment shown an irrigant cut-off button 28 biased to the extended (closed) position, shown in FIG. 3, by a spring 28b. The button 28 is disposed slidably within the seat 28a, which may for example be formed by a bore extending generally radially through the proximal end of the elbow 24. The button 28 provides a bore 28c oriented axially (relative to the irrigant passageway 22) which, when the button 28 is depressed to the open position, wherein the bore 28c is aligned with the irrigant passageway 22 as best seen in FIG. 2, irrigant is permitted to flow to the distal end of the elbow 24. Hydraulic seals 28d (shown in FIGS. 2 and 3) retain fluid within the irrigant passageway 22. It will be appreciated that the actuator may be any mechanical or electrically-actuated means for selectively blocking and opening the irrigant passageway 22, and disposed at any suitable position along the irrigant passageway 22, and the invention is not intended to be limited to the specific actuator described and illustrated herein.

Figure 4A:
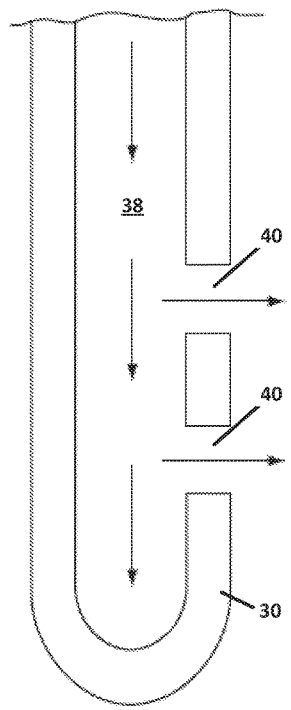
Figure 8:
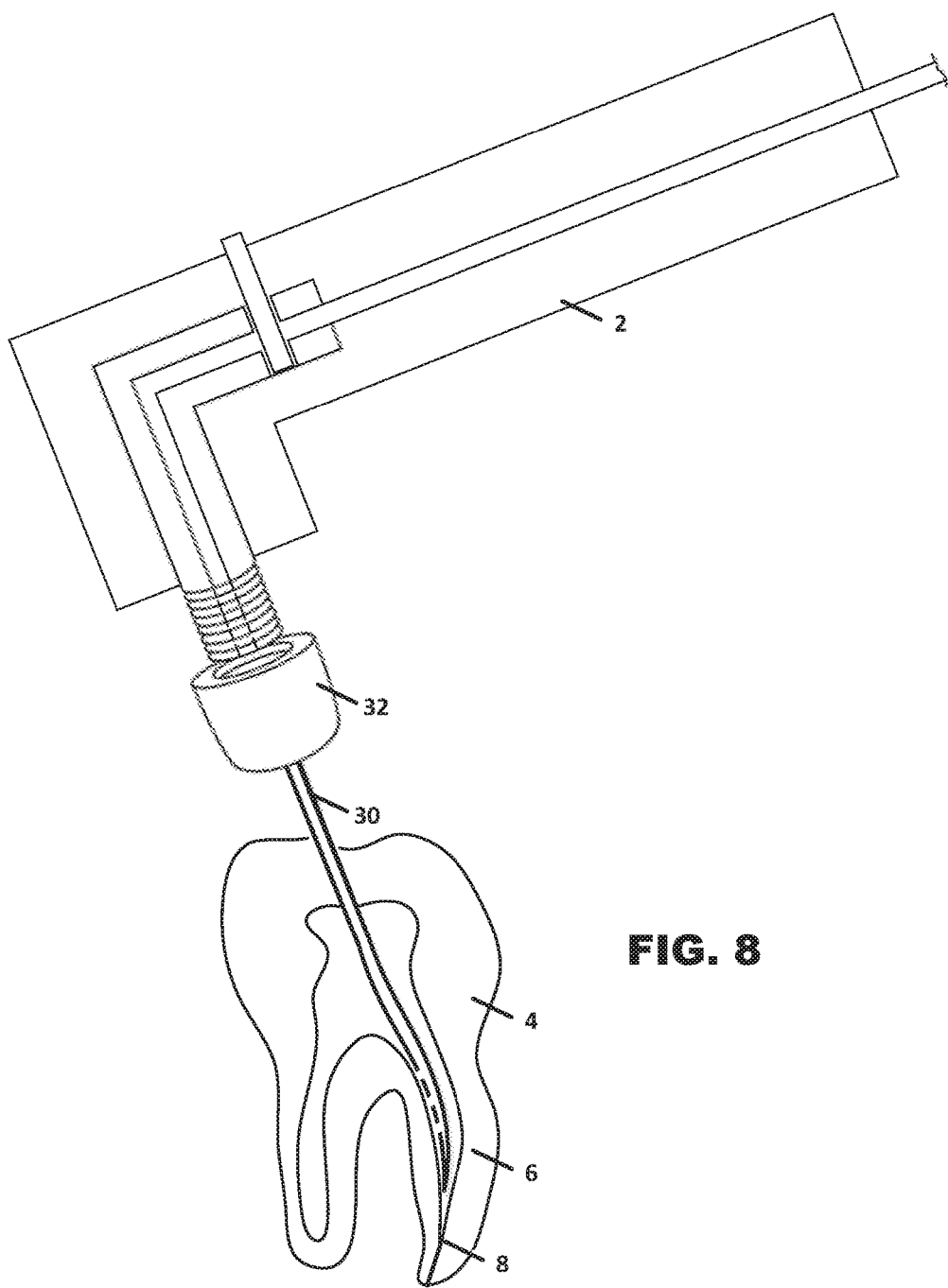
FIG. 8 is a side elevation of the tip of a needle for the device of the invention inside a root canal.

The irrigant flows through the wand 20 into the irrigant delivery needle 30, which is flexible and preferably closed at the distal tip to prevent the extrusion of the irrigant beyond the apex 8 of the root 6 of the tooth 4, shown in FIG. 8. The irrigant delivery needle 30 has one or more lateral irrigant dispersion orifices for the egress of irrigant into the canal, as described in greater detail below. The needle 30 in FIG. 1 may be typically formed from stainless steel or a nickel-titanium alloy with a thickness sufficient to withstand the pressure of the water jet while being sufficiently flexible to negotiate the canal. The needle 30 comprises a lumen 38, for example as shown in FIGS. 4A and 4B, which as noted above is preferably (but not necessarily) closed at the apex of the distal tip of the needle 30.

The needle 30 may be made available in different lengths, optionally with different external diameters which allow it to reach the apical (distal) tip of the canal while avoiding an interference fit (i.e. remaining free to move in the canal), and different lumen diameters to respectively accommodate different canal configurations and dimensions and different irrigant flow rates (for example, a constricted internal needle diameter may be used to inherently set an upper limit to the irrigant flow rate through the needle 30, as will be discussed in more detail below). The diameter of the needle at its tip should allow the needle to reach the apex of the root without extruding or abrading the surrounding tissues. In the preferred embodiments a series of needles with different diameters are available to accommodate different canal sizes and topologies.

The lumen 38 is in fluid communication with a series of irrigant dispersion orifices 40 spaced along the irrigant egress zone 36 at the tip of the needle 30. The irrigant dispersion orifices 40 are shown in FIGS. 4A and 4B as evenly spaced along one side of the needle 30, however various configurations, positioning and spacing of the irrigant dispersion orifices 40 are possible, as long as the irrigant egress zone 36 is confined within the canal space so that irrigant egresses only into the canal space and only overflow irrigant exits the tooth, to avoid damaging soft tissue within the patient's mouth.

Figure 5:
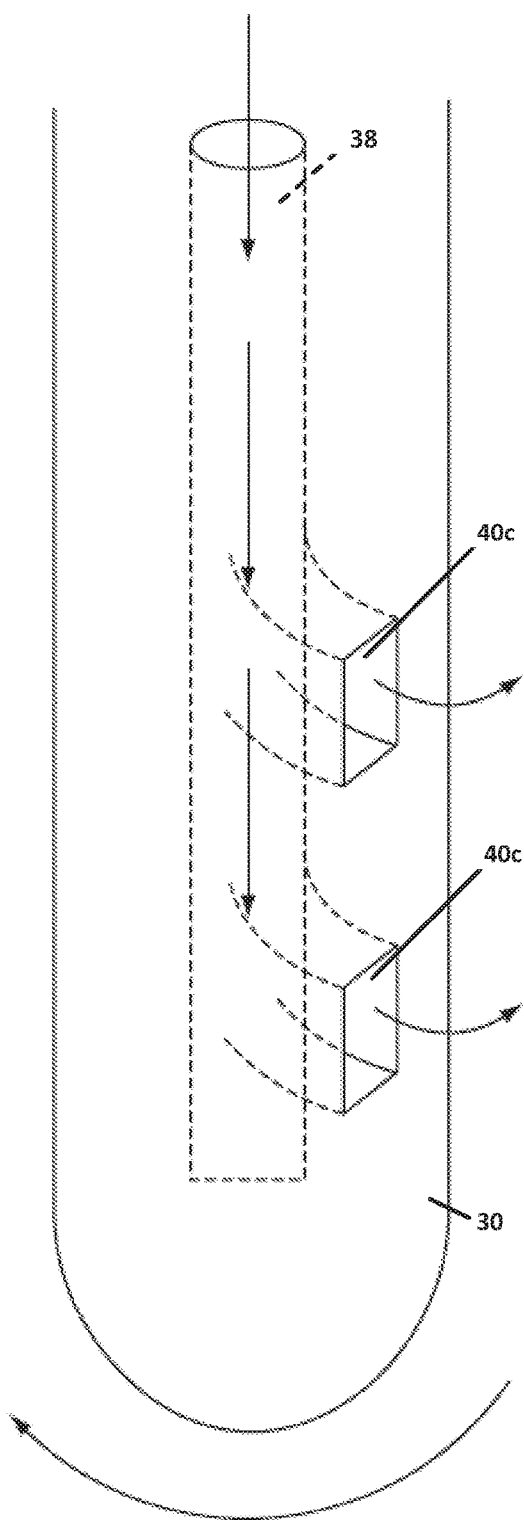
FIG. 5 is an elevation of the irrigating instrument of FIG. 4A.

The diameters of the irrigant dispersion orifices 40, the number of irrigant dispersion orifices 40, and the positions, orientations and spacing of irrigant dispersion orifices 40, can differ as between different needles 30. FIGS. 4 to 6 illustrate, by way of non-limiting example only, some possible configurations, positions and orientations of the irrigant dispersion orifices 40.

For example, FIGS. 4A and 4C illustrate the irrigant dispersion orifices 40 shown in the needle 30 of FIG. 1. In this embodiment the irrigant exits the needle 30 generally radially, shooting jets of irrigant against the canal wall to abrade away organic matter, including the pre-dentine layer, and clean the canal wall. In this embodiment the practitioner can manually rotate the wand 20 to abrade the full circumference of the canal wall as needed (not all areas of the canal wall will require the same amount of abrasion in order to remove organic debris, which may be thicker on and/or more stubbornly adhered to some parts of the canal wall than to others). This embodiment is also particularly suitable for use with embodiments in which the coupler 26 can rotate about bearings similar to those found in dental handpieces such as pneumatic wands, for example without limitation the S-Max M 600L (trademark) turbine wand sold by NSK.

Alternatively, in embodiments where the connector 26 can rotate, for example in the case of Luer-Lock quick-connect couplers, the shape and the direction of the orifices 40 in the needle 30 can be designed so that the energy of the irrigant exiting the needle 30 will rotate the needle 30 attached to the rotating distal end in a direction opposite to the direction of irrigant flow out of the dispersion orifices 40. Such an embodiment is illustrated in FIG. 5, which shows the needle 30 having a thick wall and orifices 40c extending through the needle wall in an arcuate configuration (as seen in cross-section), so that irrigant egresses from the orifices 40c at an angle tangential to the outer surface of the needle 30. The equal and opposite reaction to the irrigant egressing from the needle 30 acts tangentially against the needle wall in this embodiment, rather than radially as in the embodiment of FIG. 4A, rotating the needle 30. The embodiment of FIG. 5 thus only requires a passive rotating coupler, because the irrigant itself will drive the rotation of the needle 30 to cover the full circumference of the canal wall. This means that fewer dispersion orifices 40 are needed in order to efficiently and effectively cover the entire canal wall, which reduces cost and means that the irrigant (because it is distributed amongst fewer dispersion orifices 40 can be delivered at a higher velocity. An alternate orifice configuration having this effect is illustrated in FIG. 6B, in which the orifices 40c are generally linear but angled relative to the cross-sectional radius of the lumen 38, so that irrigant similarly egresses from the orifices 40c at an angle tangential to the outer surface of the needle 30.

FIG. 4B illustrates a variation of the above embodiments, in which the irrigant dispersion orifices 40b are disposed at an acute angle relative to the axial direction of fluid flow. Irrigant egressing through the orifices 40b thus strikes the canal wall at an upward angle in this embodiment, which can assist in dislodging organic matter and debris, and flushing them out of the canal space. This also helps to prevent the extrusion of the irrigant beyond the apex 8 of the root 6.

Figure 6A:
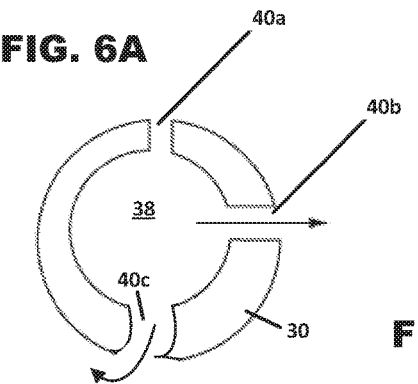
FIGS. 6A and 6B are cross-sectional plan views of different embodiments of irrigating instruments for the device of the invention.
Figure 6B:
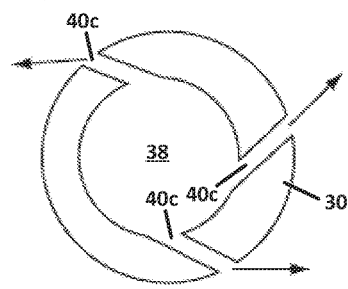
Figure 7:
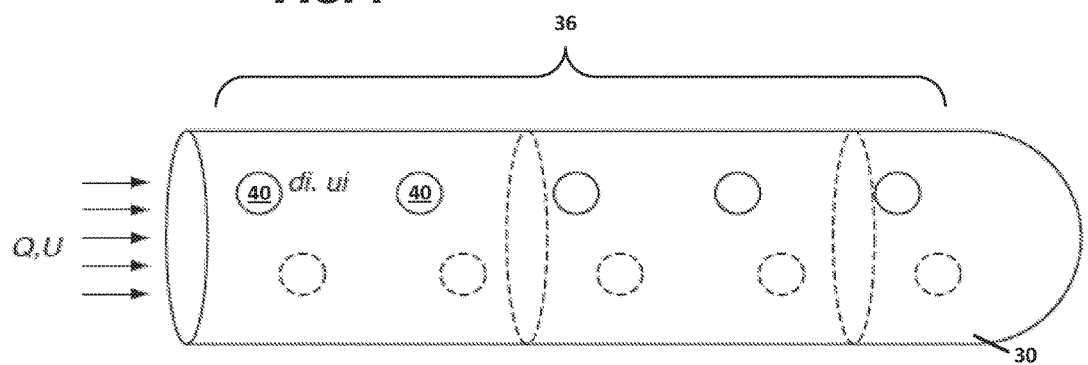
FIG. 7 is a partial cross-sectional elevation of the tip of an irrigating instrument showing irrigant flow rates through a perforated irrigating instrument.

FIG. 6A illustrates an embodiment with orifices 40a similar to the embodiment of FIG. 4A, but in which the irrigant dispersion orifices 40 are disposed along three irrigant egress zones 36 disposed at generally 90 degree intervals about the circumference of the tip 34 of the needle 30. In this embodiment the irrigant dispersion orifices 40 do not need to be the same type; a combination of different sizes, configurations and/or orientations of orifice may be used, for example irrigant dispersion orifices 40a, 40b and 40c may each be disposed along a different irrigant dispersion zone 36 in the needle 30 of FIG. 6A, to produce high pressure irrigant jets that attack the canal wall at different angles. As in the previous embodiments, this embodiment may be actively rotated by a pneumatic system (or otherwise) rotating the head of the wand 20; passively rotated by the angle at which the irrigant jets egress from the dispersion orifices 40; or manually rotated by the practitioner physically manipulating the wand 20 to cover the entire circumference of the canal wall over the course of the debridement and canal enlargement stages.

The system of the invention preferably operates off a standard mains supply voltage and activated by a master on/off power switch. The system of the invention can alternatively be modified to be integrated into existing dental equipment.

The wand 20 may be provided with an internal anti-retraction valve or a no-retraction system to prevent the retraction of oral fluids into the irrigant flow passage 22 and/or the tubing 14, if this is not provided elsewhere in the device (for example, in the couplers 18, 26 or via a positive displacement peristaltic pump or the like).

In operation, the reservoir (not shown) in the console 10 is filled with the desired irrigant, for example water or a chemical irrigant solution, and the irrigant delivery needle 30 is securely affixed to the head of the wand 20. The console 10 is set to the desired pressure and the pump 16 (if any) is activated. When the button 28 is depressed to bring the bore 28c into alignment with the irrigant passageway 22, the irrigant will flow through the tubing 14 into the needle 30. When the irrigant begins to flow (by depressing button 28 or by activating any other means) the energy stored in the pressurized, stagnant irrigant will be converted into kinetic energy.

The irrigant, which for purposes of the explanation that follows will be presumed to be incompressible and to have a constant density, flows at a specific determinable mass flow rate. The lumen 38 has a smaller diameter (d) than the diameter of the tubing (D). By virtue of the principle of mass conservation and incompressibility, when the actuator is actuated to allow irrigant to flow through the irrigant passageway 22, the pressure at the needle inlet (U) will be higher than the pressure in the tubing 14 upstream of the wand 20.

The irrigant will then be delivered into the canal space through the irrigant dispersion orifices 40. Preferably there is a plurality of irrigant dispersion orifices 40. Taking an irrigant dispersion zone 36 with 10 orifices of diameter $d_n$, by way of non-limiting example and for purposes of explanation only, in the preferred embodiment the cumulative orifice area $d_i$ is less than the diameter D of the tubing 14, i.e.:

$$d_i = d_1 + d_2 + \ldots + d_{10} < D$$

(While viscous losses exist throughout the needle, they may be neglected and/or reduced during the manufacturing process of the needle.) At the outset, the mass flow rates Qi through the orifices 40, with orifices 40 of equal diameter in this example, can also be taken as equal, i.e. $Q = Q_1 + Q_2 + \ldots = Q_{10}$. But the total mass flow rate $Q = Q_1 + Q_2 + \ldots = Q_{10}$ which implies that the mass flow rate through each orifice is one tenth of that at the needle inlet.

With the mass flow rate at each orifice known, the velocity ui at each of the orifices 40, equal to the mass flow rate divided by the orifice surface area, can then be determined $$u_i = 10 * \tfrac{1}{2}\pi d_i^2 = 5\pi d_i^2$$

Because one of the main goals of canal preparation is to dislocate debris and biofilm on the surface of the canal wall, one must produce high-velocity jets through the irrigant dispersion orifices 40. Based on the above equation for the orifice velocity $u_i$, this can be accomplished by either increasing the total mass flow rate Q or decreasing the orifice diameter $d_i$. Decreasing the orifice diameter $d_i$ is preferable since the velocity is inversely proportional to the square of the diameter compared to its linear dependence on the flow rate. In other words, if the flow rate is doubled, the velocity will increase by a factor of two, whereas reducing the orifice diameter $d_i$ by one-half increases the velocity by a factor of four.

As noted above, the orifices 40 in a particular needle 30, and/or in a particular irrigant egress zone 36, can also have different diameters. As a non-limiting example, for safety purposes the orifices 40 near the tip 34 of the needle 30 can be larger than the orifices 40 closer to the coupler 32, to produce a lower velocity through the orifices 40 at the tip 34 which is near the apical opening of the canal on the root surface. Where a needle 30 has a plurality of irrigant egress zones 36, particularly where the configuration of orifices 40 in each egress zone 36 is different, the relative sizes of the orifices 40 in each egress zone 36 can be selected so as to provide more pressure out of orifices 40 having a certain configuration—for example a tangential angle relative to the surface of the needle 30, which can rotate the needle 30—than out of the other orifices 40 which are merely removing organic debris.

Although the device 2 of the invention will not prepare the canal to a specific shape, the obturation procedure can be easily modified to adapt to the shape of the canal following the use of the device 2 of the invention.

Debris and obturation material always remain in the hard-to-reach areas of the canal (and also in the main canal) following a conventional retreatment procedure. The new invention will allow a better cleaning of canals, optimizing the removal of the remaining debris and obturation material, during a root canal retreatment procedure especially in the hard-to-reach areas of the canals.

Figure 9:
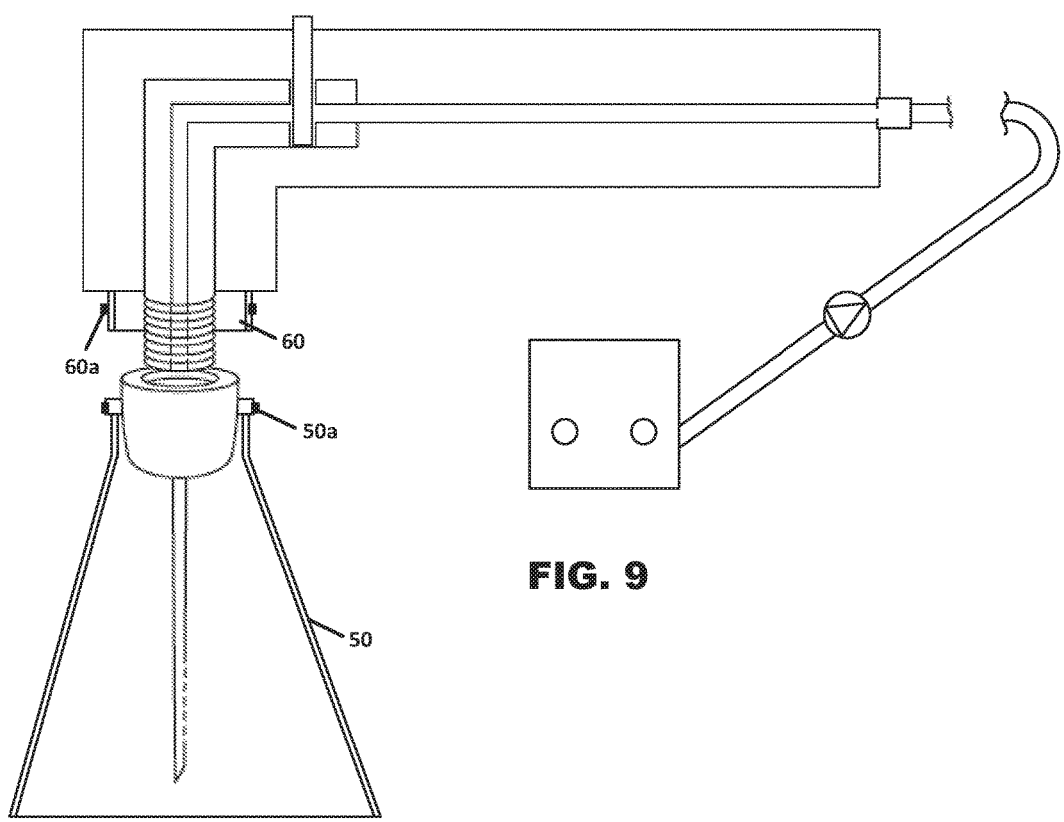
FIG. 9 is a cross-sectional elevation of a hand-held irrigation device in accordance with an embodiment of the invention providing a shield surrounding the irrigating instrument.

As illustrated in FIG. 9, the device 2 may be provided with a transparent shield 50 that extends to cover the irrigant egress zone(s) 36 of the instrument 30, to prevent possible injury to the patient, dentist or other persons present during the procedure if the irrigant flow is inadvertently activated while the needle 30 is outside of the canal. The shield can be releasably affixed to the device 2, for example by a collar 50a of the shield 50 engaged in snap-fit relation to an annular bead 60a provided on a collar nut 60. The collar nut 60 may be threaded to the male coupler portion 26 before the female coupler portion 32 is attached to the device 2.

The shield 50 can be any suitable shape, for example a cone as in the embodiment illustrated, and must be strong enough to withstand the force of the jets of irrigant egressing from the orifices 40. The shield is preferably flexible so as to be collapsible or retractable, such that it will fold back when contacting the top surface of the tooth during the insertion of the tip 34 of the instrument 30 into the canal. A thick ply or multiple-ply flexible plastic sheet may be suitable for this purpose). The shield 50 is preferably disposable for sanitary reasons, but may alternatively be composed of a material that will withstand conventional sanitizing procedures (for example autoclaving).

Figure 10:
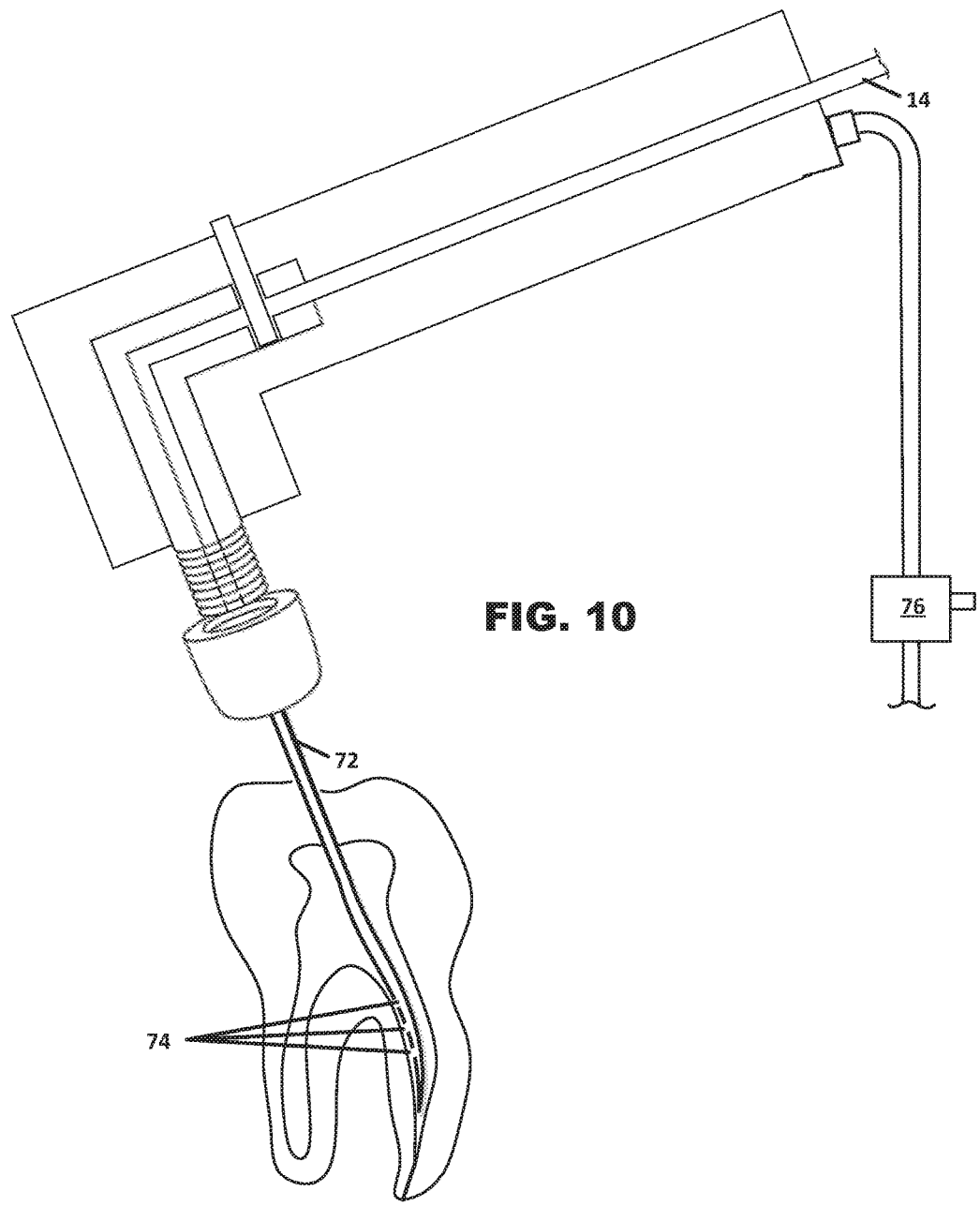
FIG. 10 is a schematic side elevation of an embodiment of the invention having an aspirating needle.

The wand may optionally be provided with an aspirating tube 70, the proximal side of which is connected to a conventional dental vacuum apparatus (not shown). The distal end of the tube 70 may be connected to an aspirating needle 72, for example in the same fashion as the irrigating needle 30 described above, which will be introduced in the canal to its tip to aspirate the fluids from within the canal at the end of the irrigation procedure. The aspirating needle 72 may have different diameters, similar to the irrigation needle 30. The aspirating needle 72 may have one or several openings 74, including lateral openings and/or an apical opening as shown in FIG. 10, with diameters large enough not to be blocked by the aspirated debris. The aspirating needle 72 may be tapered to allow for a larger internal diameter to avoid blockage of the needle 72 by aspirated debris. A silicone cap 80 can be mounted in a similar manner to the transparent shield 50 described above. The silicone cap 80 provides a good seal on the tooth 4, and consequently a strong aspirating effect in the canal once the vacuum device is activated. As an alternative to the silicone cap, the dentist can apply a fast polymerizing silicone material on the crown of the tooth 4 after the aspirating needle 72 is inserted into the canal to obtain an adequate seal. The tubing 70 is preferably disposed though the wand and wide enough to avoid blockage by aspirated material.

Figure 11:
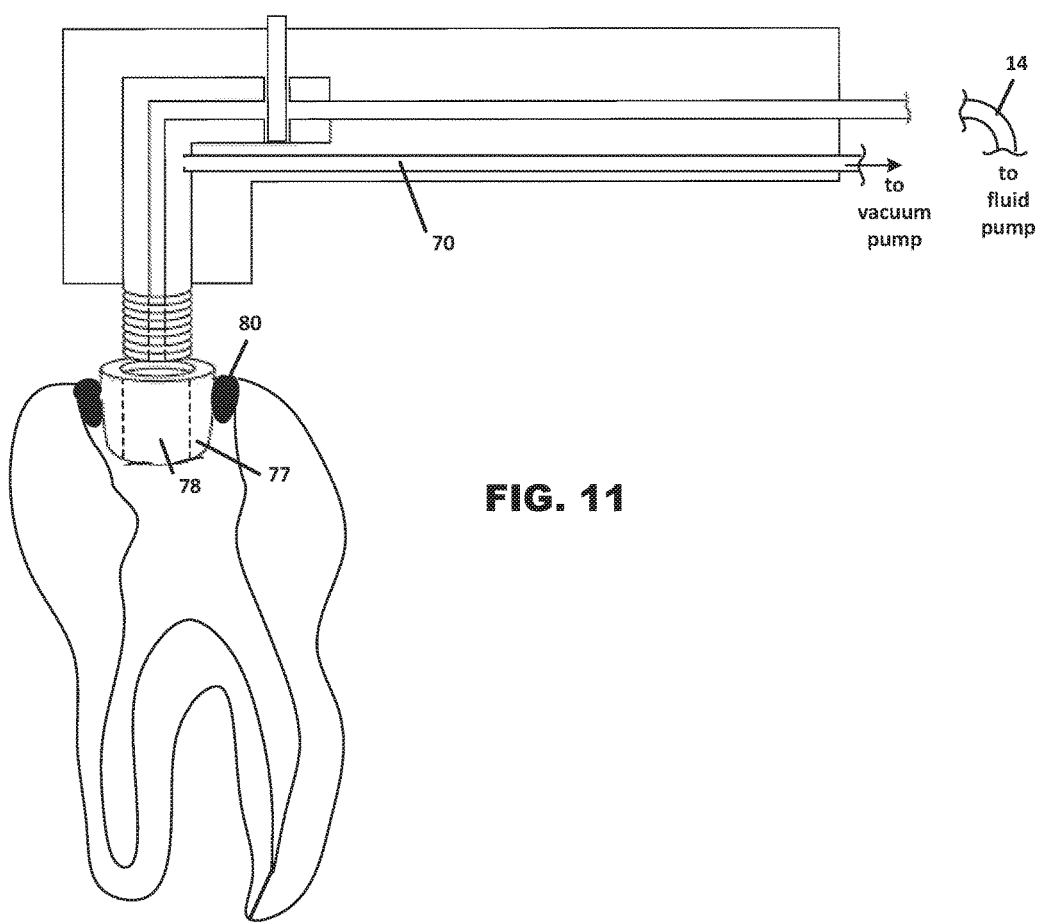
FIG. 11 is a side elevation of an embodiment of the invention utilizing the instrument coupler for aspirating the canal.

As an alternative to the aspirating needle 72, a coupler 77 may be positioned in the crown of the tooth, as shown in FIG. 11. Its lumen 78 and tube 70 should be large enough to allow aspiration without blockage. A silicone cap or fast-curing polymer 80 may be used as described above to obtain a seal and a strong vacuum effect.

As with the water supply tubing 14, the vacuum tubing 70 may attach to the vacuum system of the dental chair or to a separate vacuum apparatus (not shown) as is conventional. A switch on the wand 20 or on the tubing 70, for example switch 76 shown in FIG. 10, allows the practitioner to activate or to stop aspiration as required.

Various embodiments of the present invention having been thus described in detail by way of example, it will be apparent to those skilled in the art that variations and modifications may be made without departing from the invention. The invention includes all such variations and modifications as fall within the scope of the appended claims.

The invention claimed is:

1. A device for irrigating a canal during a root canal treatment or retreatment, comprising
    a fluid reservoir in fluid communication with at least one pump for delivering an irrigant under pressure,
    a hand-held wand having a receiving end for receiving the irrigant under pressure, and a head in fluid-tight communication with the receiving end via an irrigant passageway,
    an actuator for selectively blocking or permitting a flow of irrigant through the irrigant passageway,
    a flexible irrigant delivery needle which, when coupled with the head of the wand, is in fluid-tight communication with the irrigant passageway, the delivery needle providing a lumen in fluid communication with the irrigant passageway and at least one irrigant dispersion orifice for the egress of irrigant into the canal disposed along a side of the needle at a delivery angle offset, at the location of the at least one irrigant dispersion orifice, from a radial or axial direction relative to the lumen, and
    a free rotating collar coupling the head of the wand with the needle,
    whereby irrigant is delivered into the canal under high pressure at the selected delivery angle,
    wherein the needle is freely-rotatable with respect to the head of the wand, and
    wherein water egressing from the at least one irrigant dispersion orifice rotates the needle in the canal.

2. The device of claim 1 wherein the at least one irrigant dispersion orifice is disposed at an oblique angle relative to the lumen.

3. The device of claim 1 wherein the at least one irrigant dispersion orifice is disposed at an angle tangential to an outer surface of the needle.

4. The device of claim 1 comprising a shield disposed about the needle to contain water egressing from the needle outside the canal.

5. The device of claim 1 further comprising an aspirating tube in fluid communication with the working end of the wand.

6. The device of claim 5 wherein the aspirating tube is in fluid communication with an aspirating needle for aspirating water from the canal.

7. The device of claim 6 wherein the aspirating tube is in fluid communication with a coupler affixed to the working end of the wand for sealing against a crown of the tooth and comprising a lumen for aspirating water from the canal.

8. A wand for connection to a fluid reservoir in fluid communication with at least one pump for delivering an irrigant under pressure for irrigating a canal during a root canal treatment or retreatment, the wand comprising
    a receiving end for receiving the irrigant under pressure, and a head in fluid-tight communication with the receiving end via an irrigant passageway,
    an actuator for selectively blocking or permitting a flow of irrigant through the irrigant passageway,
    a flexible irrigant delivery needle which, when coupled with the head of the wand, is in fluid-tight communication with the irrigant passageway, the delivery needle providing a lumen in fluid communication with the irrigant passageway and at least one irrigant dispersion orifice for the egress of irrigant into the canal disposed along a side of the needle at a delivery angle offset, at the location of the at least one irrigant dispersion orifice, from a radial or axial direction relative to the lumen, and
    a free rotating collar affixed to the head of the wand coupling the wand with the needle,
    whereby irrigant is delivered into the canal under high pressure at the selected delivery angle
    wherein the needle is freely-rotatable with respect to the head of the wand, and
    wherein water egressing from the at least one irrigant dispersion orifice rotates the needle in the canal.

9. The device of claim 8 wherein the at least one irrigant dispersion orifice is disposed at an oblique angle relative to the lumen.

10. The device of claim 8 wherein the at least one irrigant dispersion orifice is disposed at an angle tangential to an outer surface of the needle.

11. The device of claim 8 comprising a shield disposed about the needle to contain water egressing from the needle outside the canal.

12. The device of claim 8 further comprising an aspirating tube in fluid communication with the working end of the wand.

13. The device of claim 12 wherein the aspirating tube is in fluid communication with an aspirating needle for aspirating water from the canal.

14. The device of claim 13 wherein the aspirating tube is in fluid communication with a coupler affixed to the working end of the wand for sealing against a crown of the tooth and comprising a lumen for aspirating water from the canal.

\* \* \* \* \*